United States Patent [19]

Smart et al.

[11] Patent Number: 5,801,057
[45] Date of Patent: Sep. 1, 1998

[54] MICROSAMPLING DEVICE AND METHOD OF CONSTRUCTION

[76] Inventors: Wilson H. Smart, 245 Washington Ave., Palo Alto, Calif. 94301; Kumar Subramanian, 6833 Corte Munras, Pleasanton, Calif. 94566

[21] Appl. No.: 620,994

[22] Filed: Mar. 22, 1996

[51] Int. Cl.⁶ ................................................. G01N 33/50
[52] U.S. Cl. ............................ 436/68; 436/95; 128/632
[58] Field of Search ........................ 436/68, 95; 128/632

[56] References Cited

U.S. PATENT DOCUMENTS 3,884,640  5/1975  Lock et al. ........................ 23/253 R
4,229,979  10/1980  Greenwood ........................ 73/704
5,525,518  6/1996  Lundsgaard et al. ................ 436/68

*Primary Examiner*—Scott W. Houtteman
*Attorney, Agent, or Firm*—Shyamala T. Rajender

[57] ABSTRACT

A minimally intrusive and less painful, self-use microsampling device and method for the measurement of glucose and other analytes in blood are provided. The device of the invention may have one or two optical windows for measuring the concentration of an absorbent reaction product or no windows if methods other than optical absorbance is used. The sampling chamber of the device can contain analytical reagents and other additives to facilitate the sampling and analytical steps. Also provided is a fabrication method for the microsampling device.

18 Claims, 4 Drawing Sheets

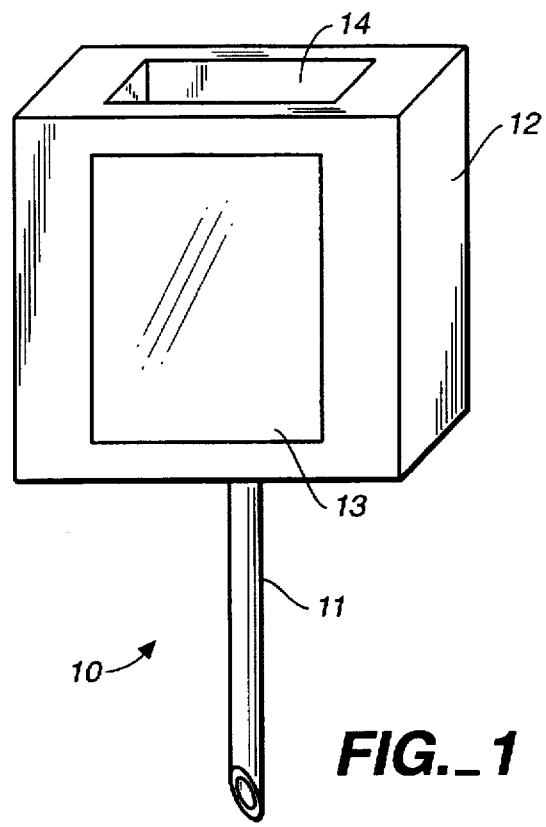
FIG._1
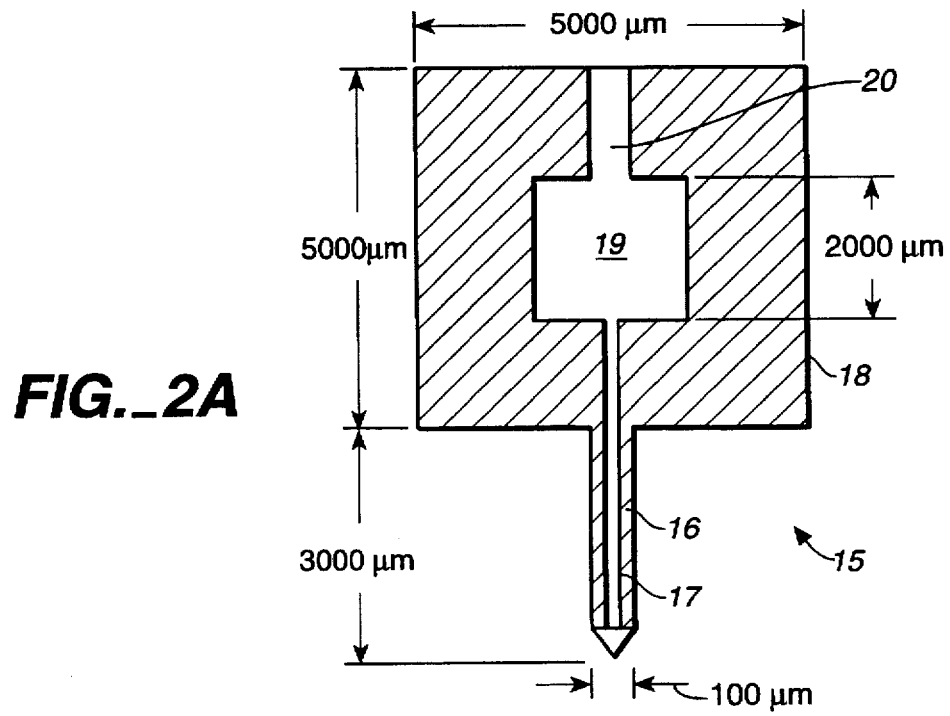
FIG._2A

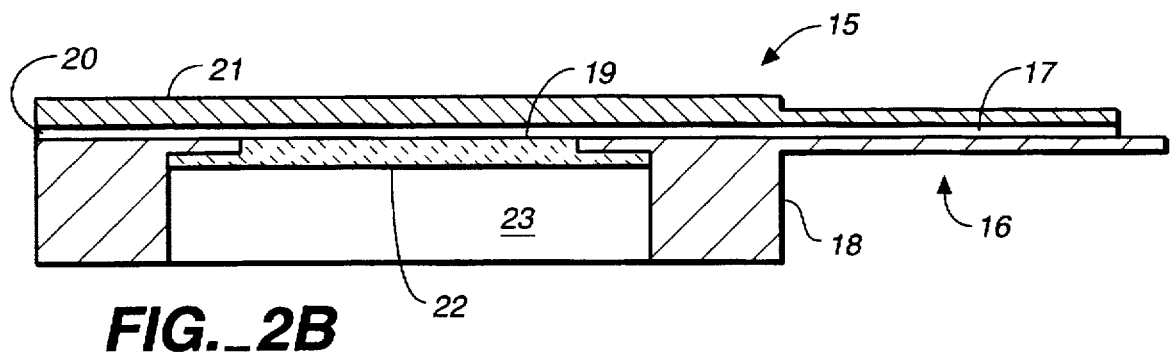
FIG._2B
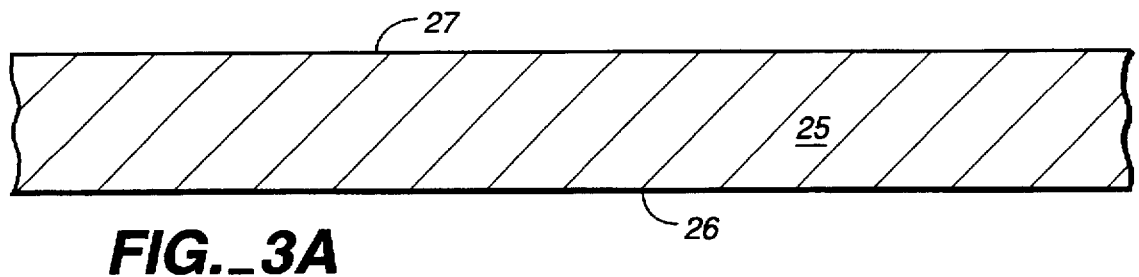
FIG._3A
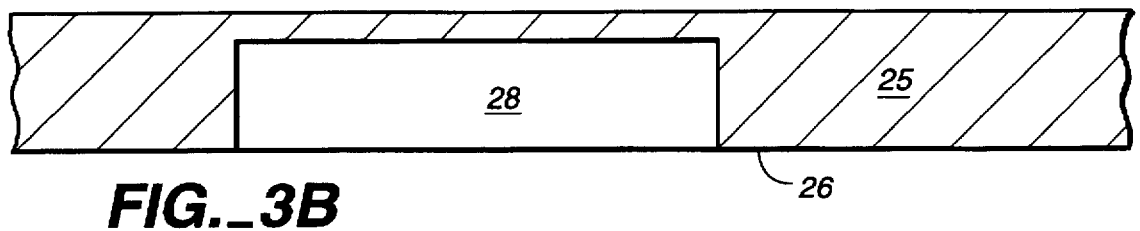
FIG._3B
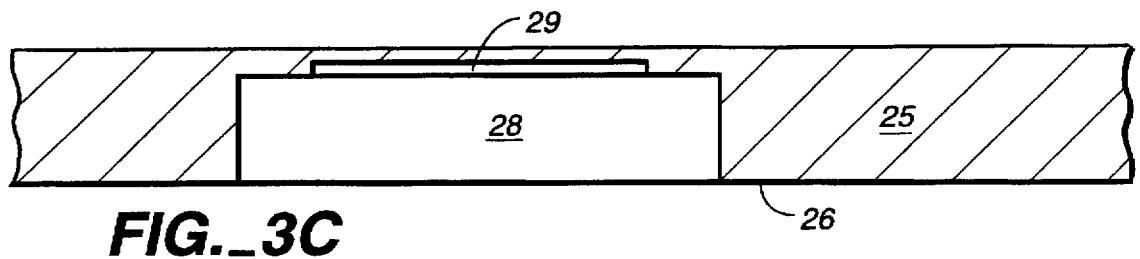
FIG._3C

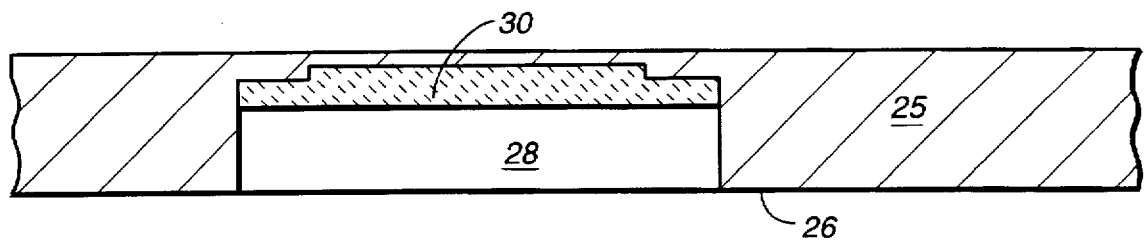
FIG._3D
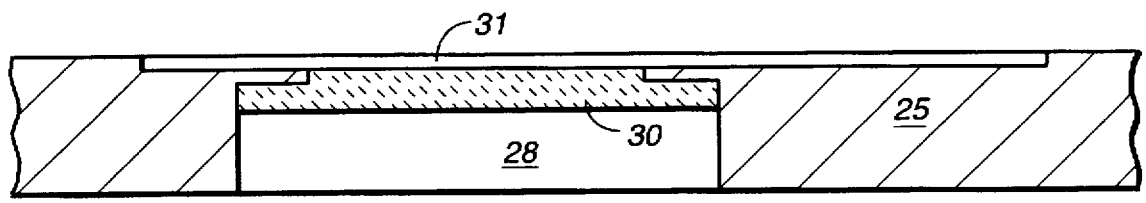
FIG._3E
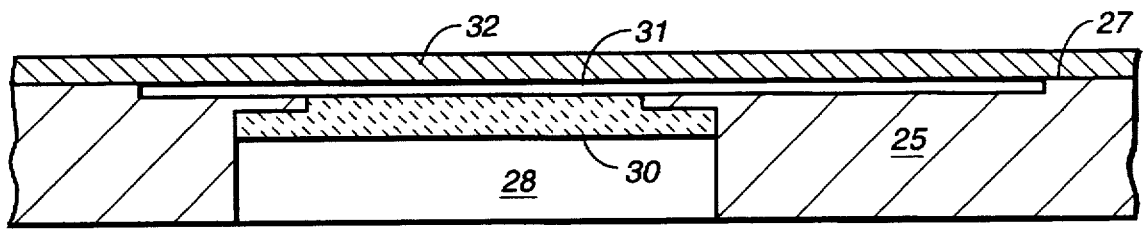
FIG._3F
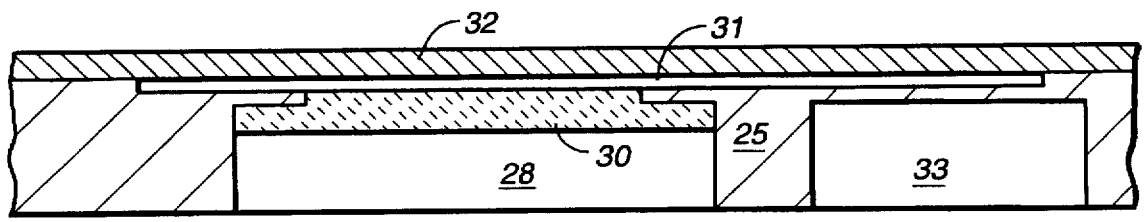
FIG._3G

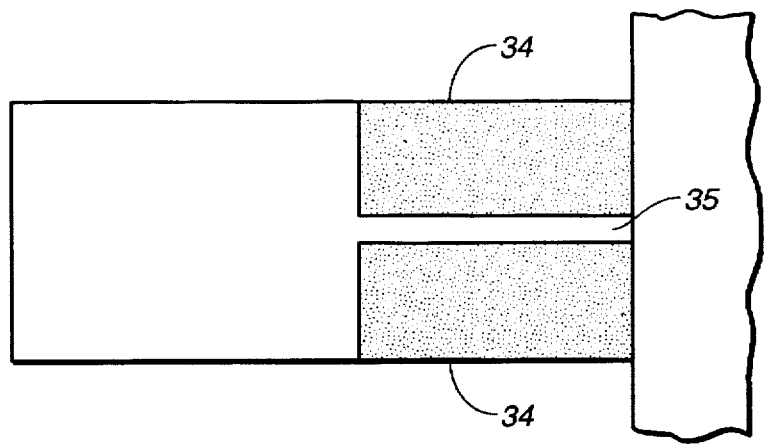
FIG._4A
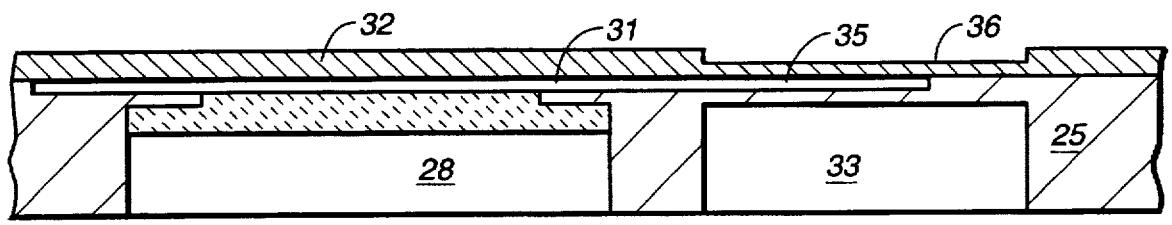
FIG._4B
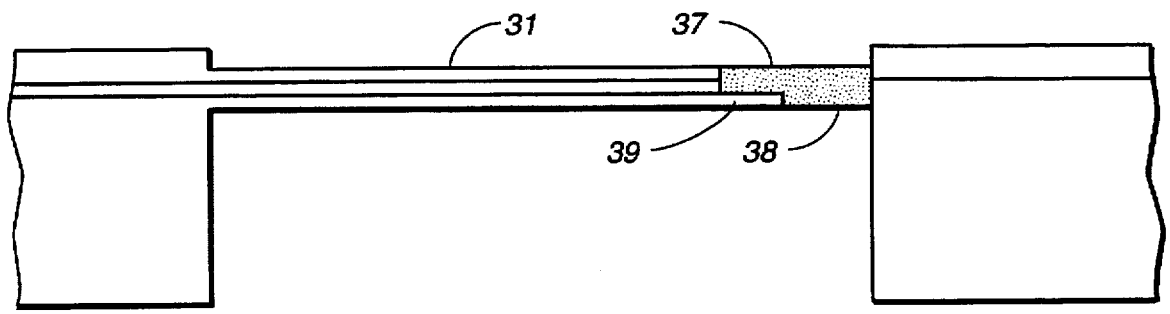
FIG._4C
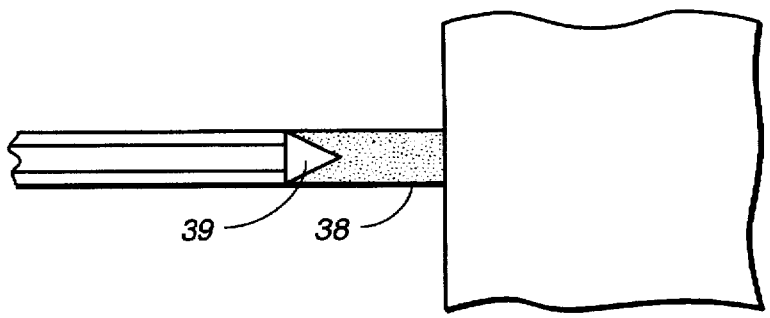
FIG._4D

MICROSAMPLING DEVICE AND METHOD OF CONSTRUCTION

FIELD OF THE INVENTION

The present invention relates to the measurement of analytes in body fluids. More specifically, it is concerned with a minimally intrusive and less painful, self-use method for the measurement of glucose and other analytes in blood.

BACKGROUND OF THE INVENTION

Diabetes mellitus is an insidious disease which affects more than 15 million Americans. About 1.5 million of these are insulin-dependent or Type I diabetics and 12 to 14 million are Type II or noninsulin-dependent. Both types of diabetes are also considered one of the most prevalent chronic conditions. Chronic, persistently high levels of glucose in the blood and in urine are characteristic of diabetes. Although glucose in the urine has been used to monitor glucose levels, the measurement of blood glucose is more reliable and logistically feasible. It has, therefore, become the most commonly followed marker for monitoring the progress of the disease and to determine treatment and control protocols. While glucose levels are monitored in doctors'offices, clinical laboratories and hospitals, the most convenient and important is the in-home or self-monitored measurement of glucose levels by the patients themselves to adjust the administration of insulin or hypoglycemics accordingly. This process is known as self-monitored blood glucose (SMBG). Normal glucose levels in the human blood have been established by various health organizations and the World Health Organization, to be in the 70–100 mg/dl range and in the 160–200 mg/dl range after a heavy meal.

As the need for hospital, laboratory and SMBG testing has been rising, diagnostic companies are offering more diabetes related testing of glucose for diagnostic and monitoring purposes. These products range from skin swabs, reagent test strips, portable electronic meters, sensors and other instruments, lancets and needles of various shapes and sizes, syringes and other paraphernalia. The most common of these include reagent strips impregnated with glucose oxidase, and packaged with portable reflectance meters. However, most of the currently available technologies, especially for SMBG measurements, are not very satisfactory because they all require some kind of lancing or finger-stick and the associated pain or sometimes even excessive bleeding. Frequent use of the method also causes calluses, impairment of the use of hands, psychological trauma and other unpleasant consequences. Studies have shown that fingertip lancing is the most painful of diabetes diagnosis and therapy even more than the self-administration of insulin by injection. The smallest lancet currently marketed is 28 gauge or an outer diameter (O.D.) of 0.017 in or 425 microns which is painfully large.

The following selected patents and articles describe past efforts in the area of the measurement of analytes in blood and other body fluids, more specifically in blood.

U.S. Pat. No. 4,935,346 "Minimum Procedure System For The Determination Of Analytes," issued Jun. 19, 1990, to Roger Phillips, Geoffrey McGarraugh, Frank Jurik and Ray Underwood, describes a method and apparatus for the measurement of glucose. The apparatus consists of an inert porous matrix one surface of which is impregnated with a reagent which reacts with the analyte to produce an optically measurable product, the analyte being applied to the other side of the matrix. The analyte migrates through the porous matrix to the reagent-coated surface and reacts with the reagent.

U.S. Pat. No. 4,627,445 "Glucose Medical Monitoring System," issued Dec. 9, 1986, to Fernando S. Garcia, Hartnut Ginnow-Merkert, Paul J. Anderson, David E. Linde and Bertram J. Hudson, discloses a hand-held pocket-sized, portable diagnostic system for measuring glucose and other components in blood. The system comprises a disposable needle or lance, a strip impregnated with a chemical reagent and other components such as a visual read-out device, photosensing circuitry and a microcomputer for process control.

U.S. Pat. No. 5,250,066 "Plastic Pointed Articles And Method For Their Preparation," issued Oct. 5, 1993, to James M. Lambert, is directed to a molded lance or needle and a handle therefor constructed out of a high-impact polymer.

U.S. Pat. No. 4,908,112 "Silicon Semiconductor Wafer For analyzing Micronic Biological Samples," issued Mar. 13, 1990, to Salvatore J. Pace, discloses a device and method for chromatographic and electrophoretic separation and detection of biological molecules. The device comprises a capillary-sized conduit formed by a channel in a semiconductor material such as a silicon crystal slab. The conduit is closed by a glass plate. Electrodes placed in the channel activate the passage of liquids through the conduit by electro-osmosis. The channel dimensions are in the range of about 100 μand is bounded by wells for containing reagents. The channels are trapezoid in shape to facilitate detection by fluorescence measurements.

U.S. Pat. No. 4,088,448 "Apparatus For Sampling, Mixing The Sample With A Reagent And Making Particularly Optical Analyses," issued May 9, 1978, to Jan Evert Lilja and Sven Erik Lennart Nilsson, relates to a sampling cuvette wherein a cavity is formed by two planar surfaces with an adjustable distance therebetween. The cuvette serves the purpose of mixing the sample with a reagent for making direct optical analyses.

U.S. Pat. No. 5,064,282 "Photometric Apparatus And Method For Measuring Hemoglobin," issued Nov. 12, 1991, to Richard H. Curtis, is directed to an apparatus and method for making a photometric absorbance measurement of hemoglobin in a blood sample. The apparatus consists of a unitary body incorporating a cuvette and an inexpensive photometer.

While the prior art devices exemplify existing methods and apparatus, there still exists a need, for noninvasive methods, or at least a less or minimally invasive and less painful method for obtaining blood samples for SMBG testing.

It is an object of the present invention, therefore, to provide a minimally invasive testing device for blood analytes.

Another object of the invention is the construction of a thin, short, fine-bore needle for blood sampling that is less painful than currently available devices.

Yet another object is to provide a method for the measurement of blood glucose levels in a minimally invasive manner.

Still another object is to provide a micro-cuvette to serve as the sampling chamber for reaction and analysis of blood analytes.

Another object of the invention is to provide a microcuvette with volumes less than one microliter.

Yet another object is to provide for an integrated needle and cuvette assembly.

Still another object is to provide an integrated unit which draws blood or other biological fluid into a microcuvette, measures the amount of the analyte such as sugar in the blood and gives out a qualitative and quantitative measure of the same all in one step.

Another object is to provide a needle of a small diameter to make the pricking of the finger tip or other areas of the skin as painless and comfortable as possible.

Additional objects, advantages and novel features of the invention will be set forth in part in the description and drawings which follow, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to a microsampling device and method for its construction.

The present invention provides a blood sampling and analyzing device using a very fine, short, hollow needle through which blood can be drawn by capillary action into a small sampling chamber, less than 1 µL in volume, where an analysis on this sample for glucose or some other biological analyte is carried out by means of a combination of chemical reagents and optical transmittance measurement. The needle and the cuvette are unitary in construction and form the disposable part of the device.

A microsampler according to the present invention comprises a microsampler chamber formed preferably out of silicon; a needle which is integral with and extending from the microsampler chamber; and a vent provided in the microsampler chamber to facilitate the flow of blood through the microbore of the needle. The microsampler chamber may be optionally provided with one or two optical windows or no optical window. The chamber and the needle may optionally include other additives which facilitate the sampling and analysis steps. A method for the measurement of glucose in blood using the microsampling device of the instant invention is provided.

Also provided is a method for the fabrication of the microsampler. The method comprises providing preferably, a silicon wafer with top and bottom surfaces, etching out two depressions in the bottom surface of the wafer, forming an optical window covering the two depressions, etching a patterned depression in the top surface aligned with the optical window in the bottom surface of the wafer and defining therein a microsampler chamber, a needle bore, and a vent channel, covering the patterned depression in the top surface of the wafer with a cover glass, etching out the needle by removing silicon and the cover glass; and forming a point on the needle.

BRIEF DESCRIPTION OF THE DRAWINGS

FIG. 1 is an overall view of the microsampling device of the present invention.

FIG. 2A is a top view of the present device.

FIG. 2B is a side view of the instant microsampling device.

FIGS. 3A to 3G represent the various stages in the fabrication process of the present microsampling device.

FIG. 4A shows the top view of the needle side etch

FIG. 4B shows glass needle etch.

FIGS. 4C and 4D are the side and top views respectively of the formation of the needle point.

DETAILED DESCRIPTION OF THE INVENTION

The present invention basically comprises a microsampling device for the measurement of biological materials from biological fluids such as glucose in blood or urine, fructosamine in the blood and the like. The device is fabricated from a silicon wafer or from other materials such as glass, ceramic, sapphire and metal. Silicon is the preferred material.

Although a silicon microfabrication technique, such as that used in the semiconductor industry consisting of photolithographic etching and deposition steps, is the preferred method used in the fabrication of the microsampling device of the present invention, other techniques such as micromachining and other types of photolithographic techniques may also be employed.

One embodiment of the microsampling device provided with two windows and method of fabrication are provided by way of description and illustration. The device with two windows is particularly suitable for detection of the analyte using transmittance photometry. The device may also be fabricated with one window where the methods of choice for the detection of the analyte may be fluorescence, luminescence or reflectance photometry. Although for purposes of illustration the device is described as having one or two windows, it may also be constructed to have no transparent or glass window and electrochemical methods used for detecting the analyte under investigation. The advantage of having no widow or one window is that the number of etching and bonding steps involved in the fabrication process and any errors associated therewith are reduced.

As shown in FIG. 1, the microsampling device or microsampler of the present invention 10 has a very fine, short needle 11 through which blood or other body fluids can be drawn into a small sampling chamber (microcuvette) 12 which preferably has a volume of less than one microliter. Sampling chamber 12 has at least one optical window 13 and a vent 14 to allow air to escape as the chamber fills when blood or other fluids are drawn in through needle 11. Needle 12 preferably has an outer diameter of 100 to 200 microns, compared to at least 425 microns for the smallest lancet currently available.

The microsampler 10 is constructed using well-established silicon microfabrication technology which has been in wide use for decades for the manufacture of electronic integrated circuits and more recently has been extended to micromechanical as well as micro-electronic devices and automobile airbag sensors. The microsampler is made by a series of very precise photolithographic, etching and very precise microdeposition steps performed on a silicon wafer. A large number of the present microsampler device can be made at the same time on a single wafer, followed by dicing to separate the individual devices, each of which is commonly referred to as a die or chip in the microelectronics industry. Each device is then sealed in an individual plastic package similar to that used to package integrated circuits.

An exemplary design of microsampler 15 is shown in FIGS. 2A and B. Needle 16 is formed as an etched channel (bore) 17 in silicon and sealed with glass cover 21 hermetically bonded to the silicon. The silicon body 18 contains a sampling chamber 19 from which needle bore 17 and vent 20 extend as an integral part thereof. The top of microsampler 15 is covered by cover glass 21 which forms an optical window for chamber 19 and also covers needle bore 17. Glass 22 deposited at the bottom of microsampler 15 forms a second optical window opposite optical window for chamber 19. Glass 22 is deposited at the bottom of a depression 23 formed in silicon body 18.

Although the needle 16 may have an outer diameter in the range of 30 to 300 microns and a bore diameter in the range of 25 to 250 microns, in the exemplary embodiment, needle 16 has an outer diameter of 100 microns, a bore diameter of 50 microns, and a length of about 3 mm. Silicon body 18 is about 5 mm×5 mm square, and chamber 19 is about 2 mm×2 mm square. Silicon body 18 has a thickness of about 500 microns to 1 mm. Chamber 19 has a depth of about 50 microns and cover glass 21 has a thickness of about 150 microns.

The initial stages or steps of the fabrication process are shown in FIGS. 3A through 3G. The microsamplers are formed in a silicon wafer 25, having a bottom surface 26 and a top surface 27, as shown in FIG. 3A. In this example, wafer 25 has a thickness of about 500 microns. Wafer 25 is a polished silicon wafer from which surface damage resulting from polishing has been removed by etching. Wafers of this type are commercially available and are commonly used in the integrated circuit industry in thickness of 500 to 1000 microns.

The bottom of wafer 25 is masked, except for a 3 mm×3 mm area for each device to be etched, and a depression or well 28 is etched for each device, to a depth of about 400 microns into wafer 25, to form a ledge for an optical window, FIG. 3B. Wafer 25 is immersed in an etch bath for this first bottom etch step. Many etchants, commonly used in the industry are suitable. If an isotropic etchant such as a mixture of hydrofluoric, nitric and acetic acids is used, there will be substantial under cutting of the mask, resulting in sloping walls. With appropriate anisotropic etchants, such as EDP (ethylene diamine, pyrocatechol and water mixture), vertical walls can be maintained. For the purpose of the present microsampler, either geometry is suitable.

In a second bottom etch step, FIG. 3C, an area of about 2 mm×2 mm in the center of the previously etched depression or well 28 is deepened to form a further depression or second well 29 which will form one window region of the microsampler 10. Following the formation of depression or well 29, a thin glass film layer 30 is deposited in the well which completely covers depression 29 and partly fills depression 28, as shown in FIG. 3D. Glass film 30 forms one window of the cuvette. To form glass film 30, a slurry of a glass-forming frit is applied to wafer 25 on the side having depressions 28 and 28. Excess slurry is removed by methods known, such as for example, with a squeegee. Wafer 25 is then heated slightly above the melting or flow temperature of the glass composition to melt the frit and cause the glass to flow and fill depression 29 and the bottom of depression 28. Because an anodic bonding step, used in a later step, requires a temperature in the range of 300° to 600° C. the frit selected must have a higher flow or melting temperature to prevent sagging of the window during the later process steps. The frit preferably has a flow temperature of about 800° C. After the bottom etch steps have been completed, a first top etch is performed next, FIG. 3E, in which a patterned depression or well 31 is etched into the top of wafer 25, by suitable masking and etching as described before, to form the cuvette chamber, the bore of the needle, and a vent channel. The pattern is similar to that shown in FIG. 2A. The etch step will remove the silicon covering the deposited glass film 30 which forms a window. At this stage, the cuvette part of the microsampler consists of one window and a cavity in silicon with a depth of about 50 microns.

A cover glass 32 is then bonded onto the top surface 27 of the entire wafer 25, enclosing the patterned depression 31. The cover glass 32 forms one surface of the cuvette and needle and comprises the second window of the cuvette. A cover glass 32 made of Corning No. 7740 composition having a thickness of 150 microns and a diameter equal to that of wafer 25 is bonded to the top of wafer 25 using an anodic bonding process, known in the art. The cover glass is positioned on top of the wafer, an electrically conducting weight having the same diameter as the cover glass and wafer is placed over the cover glass, and the assembly is heated to a temperature in the range of 300° to 600° C. A DC voltage of 400 to 800 V is applied between the weight and the wafer with the wafer connected to the negative terminal of the power supply. The initial value of the current is noted and the process is terminated when the current has fallen to 10% of its initial value, usually within 1 to 5 min. The bond is hermetic, with the bond strength exceeding that of silicon or glass and there is no significant change in the dimensions of either the glass or the silicon. Thus, the optical path length in the cuvette is not changed and is equal to the depth of the patterned depression formed by the first top etch, e.g., about 50 microns. The ability to produce a hermetic seal without affecting the dimensions of the cuvette path length is a significant advantage of the anodic bonding process. In contrast, other bonding processes which involve fusion of one of the parts at the bonding surface, or an interfacial gasket material which forms the bond, result in changes in the path length thereby creating an uncertainty concerning the calculated or desired path length of the finished microsampler.

Silicon is next removed from the bottom of wafer 25 in the region of the needle, producing depression or well 33, to form the bottom part of the needle as shown in FIG. 3G. The wafer 25 is masked on the bottom except for a 3 mm×5 mm area in the needle region of the device. The masked wafer is immersed in an etch bath for a sufficient time to remove about 425 microns of silicon to form depression 33. This step produces a wall thickness of about 25 microns at the bottom of the needle section.

FIGS. 4A–D illustrate the final stages of the microsampler fabrication process. In the needle side etch step, excess silicon is removed from regions 34 on the sides of the needle, from the bottom of the wafer, FIG. 4A. The wafer is again masked except for tile silicon to the sides of the needle (which forms the side walls of the needle) and the rest of the silicon is etched away to expose the cover glass.

Excess glass is also removed from the top of the wafer over the needle 35, to form depression 36, to thin the cover glass 32 and form the top part of the needle, as shown in FIG. 4B. The wafer is again masked except for a 3 mm×5 mm region on the top of the cover glass over the needle, and the glass is thinned by etching in hydrofluoric acid to reduce the thickness from about 150 microns to about 25 microns.

The excess glass, i.e., the remaining portion of the cover glass to the sides of the needle is also etched away, matching the silicon removal shown in/figure 4A.

The needle point is then formed, FIGS. 4C and 4D, by etching away the thinned glass over the needle point, i.e., from region 37, and etching away the silicon sides and thinning the silicon so that channel 31 is opened at the end, i.e., region 38, thereby forming needle point 39 in the silicon. Glass and silicon separating the needle point from the next device are also removed.

While the described exemplary embodiment of the present microsampling device is provided with two windows transparent to uv, infra-red or visible light, the device can also be constructed with one window or no window if transmittance spectroscopy is the not the method of choice for the detection of the analyte. For example, if a reflectance, fluorescence or luminescence measurement is used to measure the concentration of the analyte, a single transparent window will suffice. If an electrochemical sensing method is employed, no transparent window is required. When there is no window provided in the device, a silicon cover rather than a glass cover is bonded to the top of the wafer by silicon-silicon bonding techniques, such as glass-frit seals, eutectic bonds, sputtered glass, spin-on glass, and silicon direct bonding, well known in the art. The steps involved in the fabrication are similar.

For a device with one window, a silicon wafer with the top surface and bottom surfaces is provided as described earlier in forming a device with two windows. A patterned depression in the top surface is then etched to define a microsampler chamber, a needle bore, and a vent channel, as described earlier. The patterned depression in the top surface of the wafer is then covered with a cover glass. The needle is then etched out by removing the silicon and the cover glass to form the point of the needle.

To fabricate a device without a window, a patterned depression is etched in the top surface to define a microsampler chamber, a needle bore, and a vent channel as previously described. The top surface of the depression is then covered with a cover of silicon material. The needle is then etched out by removing silicon and silicon cover and forming the point of the needle.

Although blood is used as an exemplary fluid in this description of the device and method, the device may also be used with other body fluids such as urine, serum, saliva etc. Blood is used as an example only and not intended to limit the device or its application to the measurements of analytes in blood only.

The cuvette and the needle part of the device may optionally incorporate or include additives or reagents which facilitate the measurement and analyses of the analytes. These additives or reagents may be coated, sprayed or otherwise deposited on the inside or outside surface or surfaces of the needle and/or the microcuvette. The analytical reagents chosen depend on the analyte desired to be measured in the body fluid and are specific to each analyte. For instance, when glucose is the analyte, the analytical reagents include glucose dehydrogenase, $NAD^+$ (the oxidized form of nicotinamide-adenine-dinucleotide), a pH buffer such as Tris buffer, phosphate or acetate buffer, a tetrazolium salt, a detergent to lyse the red cells and diaphorase. The tetrazolium salt of choice is 3-(4,5-dimethyl-2-thiazolyl)-2,5-diphenyl-2H-tetrazolium bromide (MTT) which reacts with NADH (the reduced form of NAD) to form MTT-formazan dye. The absorbance of MTT-formazan in the 640 to 650 nm range is measured spectrophotometrically to determine the concentration of glucose in the sample. While MTT is an exemplary compound other tetrazolium salts which form formazan dyes absorbing in the desired spectral range, may also be utilized. It is important that when glucose levels in blood are being measured, the absorption region of the resulting dye (from the glucose-reagent reaction) is sufficiently outside the spectral region for hemoglobin to minimize interference by hemoglobin. A tetrazolium salt-formazan dye system is thus most suitable for glucose determination.

In addition to the specific analytical reagents, other additives or aids to the sampling procedures may also be incorporated into the cuvette and/or needle part of the device. Such additives or aids include but are not limited to, anticoagulants such as EDTA (ethylenediamine-tetraacetate), heparin, sodium fluoride, sodium citrate and the like, inside the cuvette and in the needle bore to prevent clotting when blood is used as the sampling fluid; lubricants such as silicones such as, for example, DOW Corning 360, a variety of fluorocarbons known in the art, polyvinylpyrrolidone, and the like, on the outside of the needle bore to facilitate its insertion; detergents such as dodecyltrimethylammonium bromide (DTAB), sodium cholate, Triton X-series such as, for example, polyethylene-p-t-octylphenol, and the like, in the needle bore to insure wetting; analgesics such as lidocaine, procaine, benzocaine, and the like at the tip of the needle to minimize the pain of insertion of the needle; and anti-inflammatory agents such as hydrocortisone, triamcinolone, betamethasone and the like, at the tip of the needle, to minimize skin irritation at the point of insertion.

In using the device for the measurement of glucose for example, the user pricks his/her finger or other suitable area of the body, and blood is drawn into the microcuvette through the needle by capillary action. The reagents in the cuvette react with the blood, lyse the red cells, and the glucose is enzymatically oxidized to form the optically readable dye formazan. The optical absorbance of the dye so formed is measured by suitable instrumentation and the glucose concentration determined from the reading by methods known in the art.

The of the present invention may form part of an assembly which includes but is not limited to sensing and measuring equipment, such as a spectrophotometer, as an integral part of the assembly, making it portable for the convenience of a one-step usage. Alternatively, the microsampling device may be remotely linked to sensing, electronic computational and readout equipment by known methods.

The foregoing description of the preferred embodiments of the subject invention have been presented for purposes of illustration and description and for a better understanding of the invention. It is not intended to be exhaustive or to limit the invention to the precise form disclosed; and obviously many modifications and variations are possible in light of the above teaching. The particular embodiments were chosen and described in some detail to best explain the principles of the invention and its practical application to thereby enable others skilled in the relevant art to best utilize the invention in various embodiments and with various modification as are suited to the particular use contemplated. It is intended that the invention be defined by the claims appended hereto.

What is claimed is:

1. A microsampler comprising:
   a wafer of material defining therein a microsampler chamber;
   a needle formed integrally with and extending from said microsampler chamber; and
   a vent channel communicating with said microsampler chamber.

2. The microsampler of claim 1 wherein said chamber is formed in a wafer of a material chosen from the group consisting of silicon, ceramic and sapphire.

3. The microsampler of claim 2 wherein said chamber is formed in a silicon wafer.

4. The microsampler of claim 3 additionally including at least one optical window formed in said microsampler chamber.

5. The microsampler of claim 4 wherein said chamber has a volume of less than one microliter.

6. The microsampler of claim 5 wherein said needle has an outer diameter of less than 300 microns and a bore diameter of less than 250 microns.

7. The microsampler of claim 6 wherein the outer diameter of said needle is 100 microns and the bore diameter is 50 microns.

8. The microsampler of claim 6 wherein said chamber has two optical windows.

9. The microsampler of claim 8 wherein said chamber includes a mixture of reagents.

10. The microsampler of claim 9 wherein said needle is coated with sampling aids.

11. The microsampler of claim 10 wherein said sampling aids include anticoagulants, lubricants, detergents, analgesics and aniti-inflammatories.

12. A method of measuring glucose in blood comprising:
   a. providing a microsampling device according to claim 7;
   b. providing in said chamber of said device a mixture of reagents comprising glucose dehydrogenase, NAD$^+$, a pH buffer, a tetrazolium salt, detergent and diaphorase to form a formazan dye when mixed with blood;
   c. pricking the finger of a user with said needle to draw blood of said user into said chamber of said device and mix with said reagents; and
   d. measuring the concentration of the glucose in the blood from the absorbance of the formazan dye.

13. The method of claim 12 further comprising coating the needle with sampling aids.

14. The method of claim 13 wherein said sampling aids include heparin, silicone, Triton, lidocaine and hydrocortisone.

15. The method of claim 14 where in said hydrocortisone is at the tip of the needle and said silicone is on the outside of the needle.

16. A method of making a microsampler with two optical windows comprising:
   a. providing a silicon wafer having a top surface and a bottom surface;
   b. etching out first and second depressions in the bottom surface of said wafer;
   c. forming an optical window in the first and second depressions;
   d. etching a patterned depression in the top surface aligned with the optical window in the bottom surface of said wafer and defining therein a microsampler chamber, a needle bore, and a vent channel;
   e. covering said patterned depression in said top surface with a cover glass;
   f. etching out the needle by removing silicon and cover glass; and
   g. forming a point on the needle.

17. A method of making a microsampler with one window comprising:
   a. providing a silicon wafer having a top surface and a bottom surface;
   b. etching a patterned depression in the top surface of said wafer and defining therein a microsampler chamber, a needle bore, and a vent channel;
   c. covering said patterned depression in said top surface with a cover glass;
   d. etching out the needle by removing silicon and cover glass; and
   e. forming a point on the needle.

18. A method of making a microsampler comprising:
   a. providing a silicon wafer having a top surface and a bottom surface;
   b. etching a patterned depression in the top surface of said wafer and defining therein a microsampler chamber, a needle bore, and a vent channel;
   c. covering said patterned depression in said top surface with a cover of silicon material;
   d. etching out the needle by removing silicon and silicon cover; and
   e. forming a point on the needle.

* * * * *